US011291797B2

(12) United States Patent
Bishawi

(10) Patent No.: US 11,291,797 B2
(45) Date of Patent: Apr. 5, 2022

(54) DRAINAGE OR INFUSION CATHETER AND METHOD OF USE

(71) Applicant: DUKE UNIVERSITY, Durham, NC (US)

(72) Inventor: Muath Bishawi, Durham, NC (US)

(73) Assignee: Duke University, Durham, NC (US)

( * ) Notice: Subject to any disclaimer, the term of this patent is extended or adjusted under 35 U.S.C. 154(b) by 422 days.

(21) Appl. No.: 16/390,291

(22) Filed: Apr. 22, 2019

(65) Prior Publication Data

US 2019/0247615 A1     Aug. 15, 2019

Related U.S. Application Data

(63) Continuation of application No. 15/810,480, filed on Nov. 13, 2017, now Pat. No. 10,307,566.
(Continued)

(51) Int. Cl.
*A61M 25/00* (2006.01)
*A61M 27/00* (2006.01)
(Continued)

(52) U.S. Cl.
CPC ........ *A61M 25/0023* (2013.01); *A61M 1/285* (2013.01); *A61M 25/007* (2013.01); *A61M 25/0041* (2013.01); *A61M 25/0102* (2013.01); *A61M 25/04* (2013.01); *A61M 27/002* (2013.01); *A61M 27/006* (2013.01); *A61M 5/158* (2013.01); *A61M 5/3291* (2013.01); *A61M 25/0108* (2013.01); *A61M 2025/0042* (2013.01); *A61M 2025/0175* (2013.01); *A61M 2205/0266* (2013.01); *A61M 2210/101* (2013.01);
(Continued)

(58) Field of Classification Search
CPC ............ A61M 25/007; A61M 25/0102; A61M 25/0041; A61M 1/285; A61M 25/0023; A61M 27/002; A61M 27/006; A61M 25/04; A61M 5/158; A61M 2210/101; A61M 5/3291; A61M 2210/1021; A61M 2210/1075; A61M 2025/0175; A61M 2210/125; A61M 25/0108; A61M 2025/0042; A61M 2205/0266
See application file for complete search history.

(56) References Cited

U.S. PATENT DOCUMENTS 3,669,094 A    6/1972   Heyer
4,365,632 A   12/1982   Kortum
(Continued)

FOREIGN PATENT DOCUMENTS

EP         0145166 B1    12/1989

*Primary Examiner* — Adam Marcetich
(74) *Attorney, Agent, or Firm* — Polsinelli PC

(57) ABSTRACT

A drainage or infusion catheter and methods of use are disclosed. In one embodiment, the catheter includes a tube body having a proximal end and a distal end, and a plurality of ports arranged along the tube body from the distal end to the proximal end. The distal end of the tube body is configured to deform around itself into a substantially spiral shape so as to cover at least one of the plurality of ports located near the proximal end of the tube body. In another embodiment, a flap is configured to erupt from apertures arranged in the tube and extend outwardly around the tube body so as to cover at least one of the plurality of ports located near the proximal end of the tube body.

20 Claims, 6 Drawing Sheets

Related U.S. Application Data

(60) Provisional application No. 62/528,737, filed on Jul. 5, 2017.

(51) Int. Cl.
| | |
|---|---|
| *A61M 1/28* | (2006.01) |
| *A61M 25/01* | (2006.01) |
| *A61M 25/04* | (2006.01) |
| *A61M 5/158* | (2006.01) |
| *A61M 5/32* | (2006.01) |

(52) U.S. Cl.
CPC .............. *A61M 2210/1021* (2013.01); *A61M 2210/1075* (2013.01); *A61M 2210/125* (2013.01)

(56) References Cited

U.S. PATENT DOCUMENTS

| | | | |
|---|---|---|---|
| 4,568,338 A | 2/1986 | Todd | |
| 5,256,146 A * | 10/1993 | Ensminger | A61M 25/04 |
| | | | 604/104 |
| 5,472,435 A | 12/1995 | Sutton | |
| 5,509,900 A | 4/1996 | Kirkman | |
| 5,523,092 A | 6/1996 | Hanson et al. | |
| 5,820,631 A | 10/1998 | Nobles | |
| 5,895,398 A * | 4/1999 | Wensel | A61B 17/22 |
| | | | 606/159 |
| 5,964,744 A | 10/1999 | Balbierz et al. | |
| 5,997,526 A | 12/1999 | Giba et al. | |
| 6,159,196 A | 12/2000 | Ruiz | |
| 6,319,230 B1 | 11/2001 | Palasis et al. | |
| 6,391,018 B1 | 5/2002 | Tanaka et al. | |
| 6,402,736 B1 * | 6/2002 | Brown | A61M 25/0017 |
| | | | 604/264 |
| 6,986,752 B2 | 1/2006 | McGuckin, Jr. et al. | |
| 7,037,288 B2 | 5/2006 | Rosenberg et al. | |
| 8,123,739 B2 | 2/2012 | McQueen et al. | |
| 8,834,464 B2 | 9/2014 | Stewart et al. | |
| 9,694,166 B2 | 7/2017 | Hurt | |
| 2002/0091352 A1 | 7/2002 | McGuckin, Jr. et al. | |
| 2002/0143302 A1 | 10/2002 | Hinchliffe et al. | |
| 2003/0144623 A1 | 7/2003 | Heath et al. | |
| 2003/0181842 A1 | 9/2003 | Gellman | |
| 2003/0191452 A1 | 10/2003 | Meglin et al. | |
| 2004/0073194 A1 | 4/2004 | Olsen et al. | |
| 2004/0127913 A1 | 7/2004 | Voss | |
| 2005/0119668 A1 * | 6/2005 | Teague | A61B 17/221 |
| | | | 606/127 |
| 2005/0165431 A1 | 7/2005 | Krivoruchko | |
| 2006/0015089 A1 | 1/2006 | Meglin et al. | |
| 2007/0010715 A1 | 1/2007 | Sixto et al. | |
| 2008/0269686 A1 | 10/2008 | Young et al. | |
| 2008/0312599 A1 | 12/2008 | Rosenberg | |
| 2009/0099527 A1 | 4/2009 | Rosenberg et al. | |
| 2009/0230167 A1 | 9/2009 | Xiao et al. | |
| 2009/0318898 A1 | 12/2009 | Dein | |
| 2011/0077644 A1 | 3/2011 | Pham et al. | |
| 2011/0282368 A1 | 12/2011 | Swayze et al. | |
| 2012/0071832 A1 | 3/2012 | Bunch | |
| 2012/0078226 A1 | 3/2012 | Latere Dwan'isa et al. | |
| 2012/0209203 A1 | 8/2012 | Gibertoni et al. | |
| 2013/0085468 A1 | 4/2013 | Buydenok | |
| 2013/0131615 A1 | 5/2013 | Riordan | |
| 2013/0158464 A1 | 6/2013 | Samoocha et al. | |
| 2013/0245637 A1 | 9/2013 | Norred et al. | |
| 2014/0336528 A1 | 11/2014 | Sethi | |
| 2015/0174375 A1 | 6/2015 | DeVries et al. | |

* cited by examiner

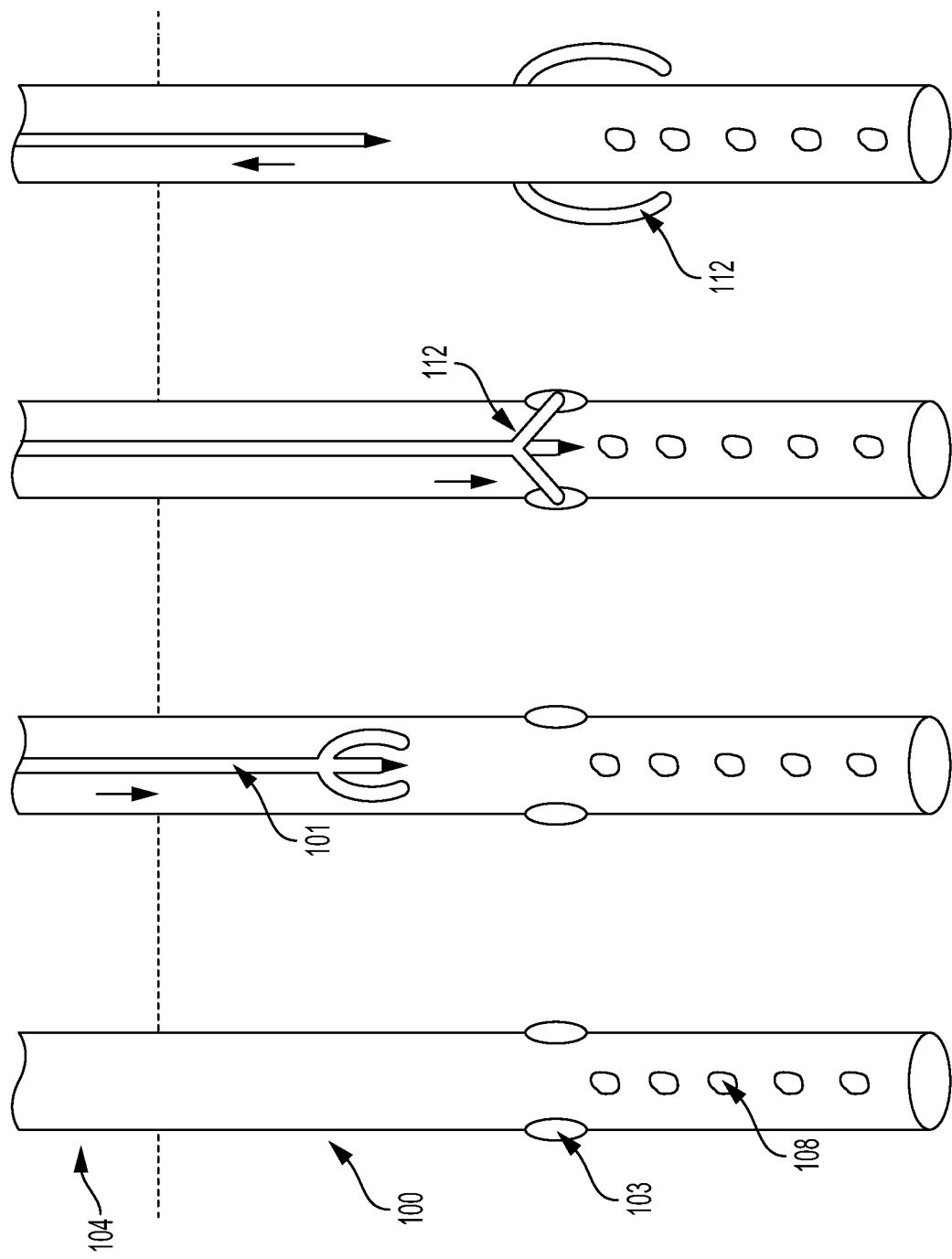

DRAINAGE OR INFUSION CATHETER AND METHOD OF USE

CROSS REFERENCE TO RELATED APPLICATIONS

The present application is a continuation of U.S. patent application Ser. No. 15/810,480, filed Nov. 13, 2017, which claims priority to U.S. Provisional Patent Application No. 62/528,737, filed Jul. 5, 2017. The entire disclosure contents of these applications are herewith incorporated by reference into the present application.

BACKGROUND

Catheters are one of the most commonly used medical devices and have application for a number of diagnostic and therapeutic procedures. The tip of current drainage or infusion systems is typically made of a sealed piece of tubing with a series of holes in the sides and/or the end. The fluid or air flows through these holes into or out of the lumen of the tubing. When choroid plexus, or other substances (blood, proteins, etc.), enters into the holes, it tends to bridge in the lumen of the tubing causing an obstruction. When the lumen of the tube is obstructed, replacement or revision is required.

Technologies that mitigate accurate placement, and decrease obstruction and/or migration can limit the distress and expenses associated with repeated catheter implantation procedures, as well as potentially reduce the chance of infection.

Thus, there is a need for a drainage and/or infusion catheter having a shape that will slow catheter obstruction. By preventing catheter obstruction, malfunctions can be greatly reduced and obviate the need for procedures or even surgery to address the catheter failure.

SUMMARY

In one embodiment, a method for inserting a drainage or infusion catheter into a cavity of a subject is provided. The method includes providing a catheter comprising a tube body defining a passageway therethrough, the tube body having a proximal end and a distal end, and a plurality of ports arranged along the tube body from the distal end to the proximal end. The distal end of the tube body is deformed around itself in a 3D shape so as to cover at least one of the plurality of ports located near the proximal end of the tube body. The method further includes inserting an introducer within the tube body of the catheter such that the 3D shape at the distal end is straightened, inserting the catheter into the cavity, and removing the introducer from the catheter such that when the introducer is removed, the distal end of the tube body re-forms into the 3D shape.

In another embodiment, a method for inserting a drainage or infusion catheter into a cavity of a subject is disclosed, the method includes providing a catheter comprising a tube body defining a passageway therethrough, the tube body having a proximal end and a distal end, a plurality of ports arranged along the tube body from the distal end to the proximal end, and at least two apertures arranged within the tube body between the distal end and the proximal end. The method further includes inserting the catheter into the cavity, and inserting an intraluminal catheter within the tube body of the catheter, the intraluminal catheter having a flap. The flap erupts from the at least two apertures and extends outwardly around the tube body so as to cover at least one of the plurality of ports located near the proximal end of the tube body.

In another embodiment, a drainage and/or insertion catheter is disclosed. The drainage and/or insertion catheter includes a tube body defining a passageway therethrough, the tube body having a proximal end and a distal end, and a plurality of ports arranged along the tube body from the distal end to the proximal end. The distal end of the tube body is configured to deform around itself into a substantially spiral shape so as to cover at least one of the plurality of ports located near the proximal end of the tube body.

In addition to the exemplary aspects and embodiments described above, further aspects and embodiments will become apparent by reference to the drawings and by study of the following detailed description.

BRIEF DESCRIPTION OF THE DRAWINGS

Exemplary embodiments are illustrated in the drawings. It is intended that the embodiments and figures disclosed herein are to be considered illustrative rather than restrictive.

FIGS. 5A-5D show the catheter of FIG. 2 being inserted into a subject.

DETAILED DESCRIPTION

For the purposes of promoting an understanding of the principles of the disclosure, reference will now be made to preferred embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

As used herein, the term "subject" and "patient" are used interchangeably herein and refer to both human and nonhuman animals. The term "nonhuman animals" of the disclosure includes all vertebrates, e.g., mammals and non-mammals, such as nonhuman primates, sheep, dog, cat, horse, cow, chickens, amphibians, reptiles, and the like. In some embodiments, the subject is a human patient that is in need of having fluid drained from an organ or tissue. In certain embodiments, the subject is a human patient suffering from hydrocephalus.

"About" is used to provide flexibility to a numerical range endpoint by providing that a given value may be "slightly above" or "slightly below" the endpoint without affecting the desired result.

Unless otherwise defined, all technical terms used herein have the same meaning as commonly understood by one of ordinary skill in the art to which this disclosure belongs.

The drainage and/or infusion catheters described herein demonstrate consistently improved resistance to occlusion. The catheter includes a deformation in the form of a 3D shape at the distal end of the tube body that, after insertion and upon withdrawal of the introducer, re-shapes into the original 3D shape. The catheter provides improved resistance to occlusion and slows catheter obstruction and drifting out of position. Such catheters can fit into the existing clinical pathway and procedure, require no extensive training, and will reduce revisions. By preventing ingrowth of tissue, catheter malfunctions can be greatly reduced and obviate the need for replacement.

Figure 1:
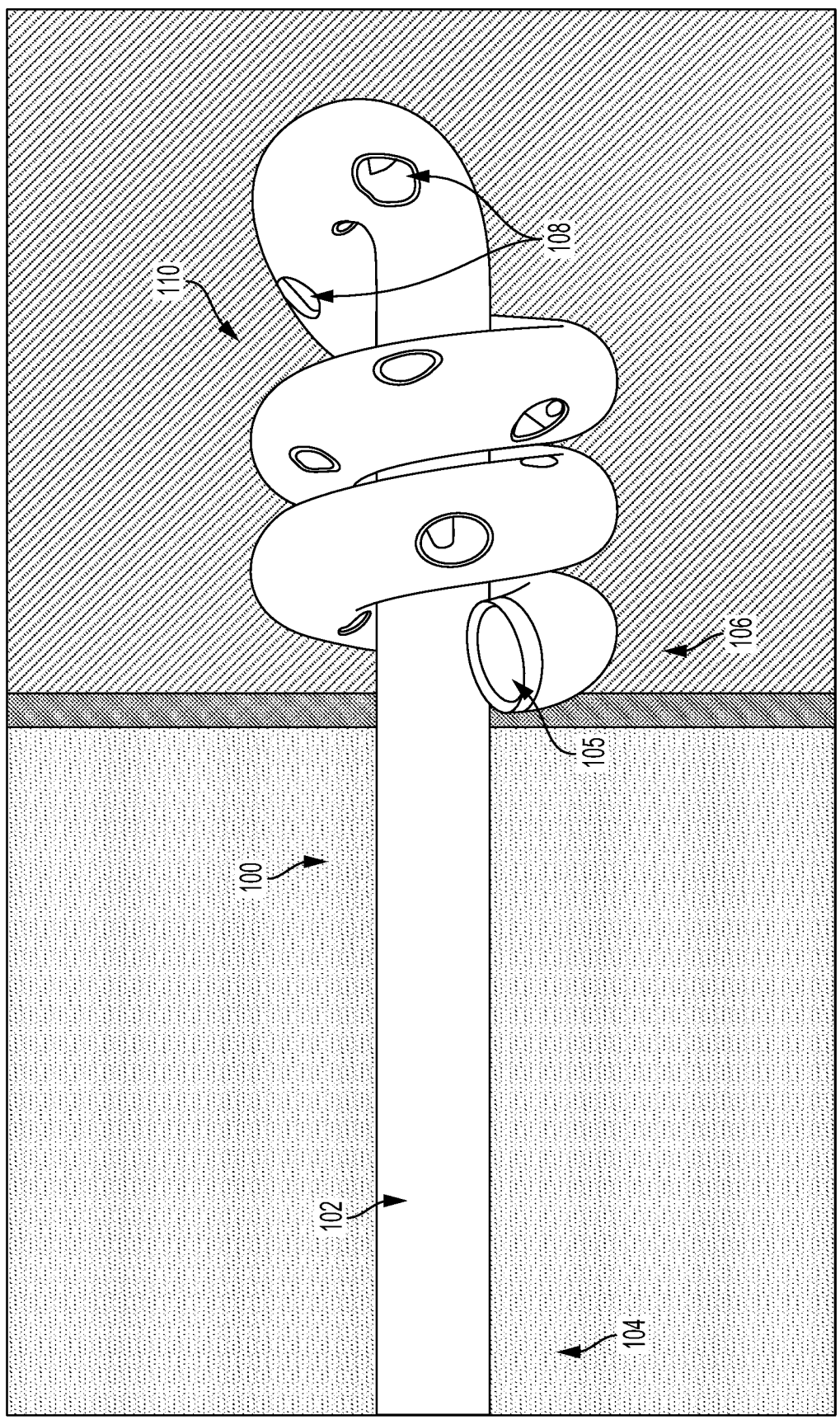
FIG. 1 is a perspective view of a catheter in accordance with one embodiment of the present disclosure.

FIG. 1 shows a drainage and/or infusion catheter 100 in accordance with one embodiment. The catheter 100 may be used for, e.g., the drainage of cerebrospinal fluid ("CSF") or pleural effusion or air from the pleural space, drainage of bile from the gallbladder, the use of peritoneal dialysis in the abdomen, the drainage of an abscess, or the drainage of urine from the bladder, the drainage or infusion of food/nutrients in the GI system as a G or J tube, or for the infusion of drugs, blood, chemotherapic agents, either in a body cavity or intravascularly either in a vein or an artery, etc. This type of catheter can also be used as part of a cannula for the circulation of blood in and out of the body. As shown in FIG. 1, the catheter 100 comprises a tube body 102 having a first or proximal end 104 and a second or distal end 106. In one embodiment, the tube body 102 comprises a tubular/circular shape. In some embodiments, the tube body 102 may define a fluid passageway 105 therethrough, and may be any length that is sufficient to provide for the insertion of the proximal end 104 into a cavity of a subject or patient. In some examples, the cavity may be a cranial cavity.

In one embodiment, the tube body 102 comprises a length of about 5 cm to about 100 cm. In another embodiment, the tube body 102 comprises an outer diameter of about 1 mm to about 80 mm. In certain embodiments, such as for intravascular or ventricular indications, the outer diameter is about 2 mm to about 3.5 mm. In another embodiment, the tube body 102 comprises an inner diameter of about 1 mm to about 40 mm. In certain embodiments, such as for drainage of a loculated collection or drainage/infusion of blood in the form of a cannula, the inner diameter is about 0.5 mm to about 2 mm.

The tube body 102 may further include a plurality of entrance ports or slots 108 that provide access to the interior portion of the tube body 102. In some embodiments, the entrance ports/slots 110 comprise a width of about 0.1 mm to about 2 mm and a length of about 1.5 mm to about 12 mm. In certain embodiments, the entrance ports/slots 108 comprise a width of about 0.2 mm to about 5 mm and a length of about 3 mm to about 20 mm.

The distal end 106 of the tube body 102 is configured to deform. In one embodiment, the distal end 106 is twisted or coiled around itself to create a 3D shape 110. In some embodiments, the 3D shape may comprise a loop, a "j", a knot, a spiral, or a coil, for example. Other suitable shapes are possible as well. The 3D shape 110 allows for the physical protection or cover of one or more of the entrance port(s) 108 located closest to the proximal end 104 of the drainage catheter 100 from being externally blocked, ultimately decreasing the amount of clogging the catheter experiences.

In one embodiment, the 3D shape 110 is made of a shape memory material which allows the distal end 106 to remain in its deformed state. In another embodiment, a wire or string (not shown) can hold the 3D shape 110 in place. In such an embodiment, a distal fixation point of the string or wire helps hold the catheter angulation under tension. Once the catheter is to be removed, the string or wire can be cut distally to loosen the tension in the skin, therefore allowing the catheter to become deformable.

Additionally, the 3D shape 110 effectively increases the surface area of the catheter that is within the cavity, which enables the tube body 102 to have more entrance ports 108. For example, in one embodiment, at least forty ports are located along the tube body 102. The existence of additional entrance ports 108 decreases the likelihood of a blockage of all of the entrance ports 108, thereby increasing the likelihood of the catheter maintaining its proper function.

Still further, the 3D shape 110 produces an anchoring shape, such as a knot, for example, which limits catheter drifting over an extended period of time, while still maintaining a shape permissible to fluid flow.

Figure 2:
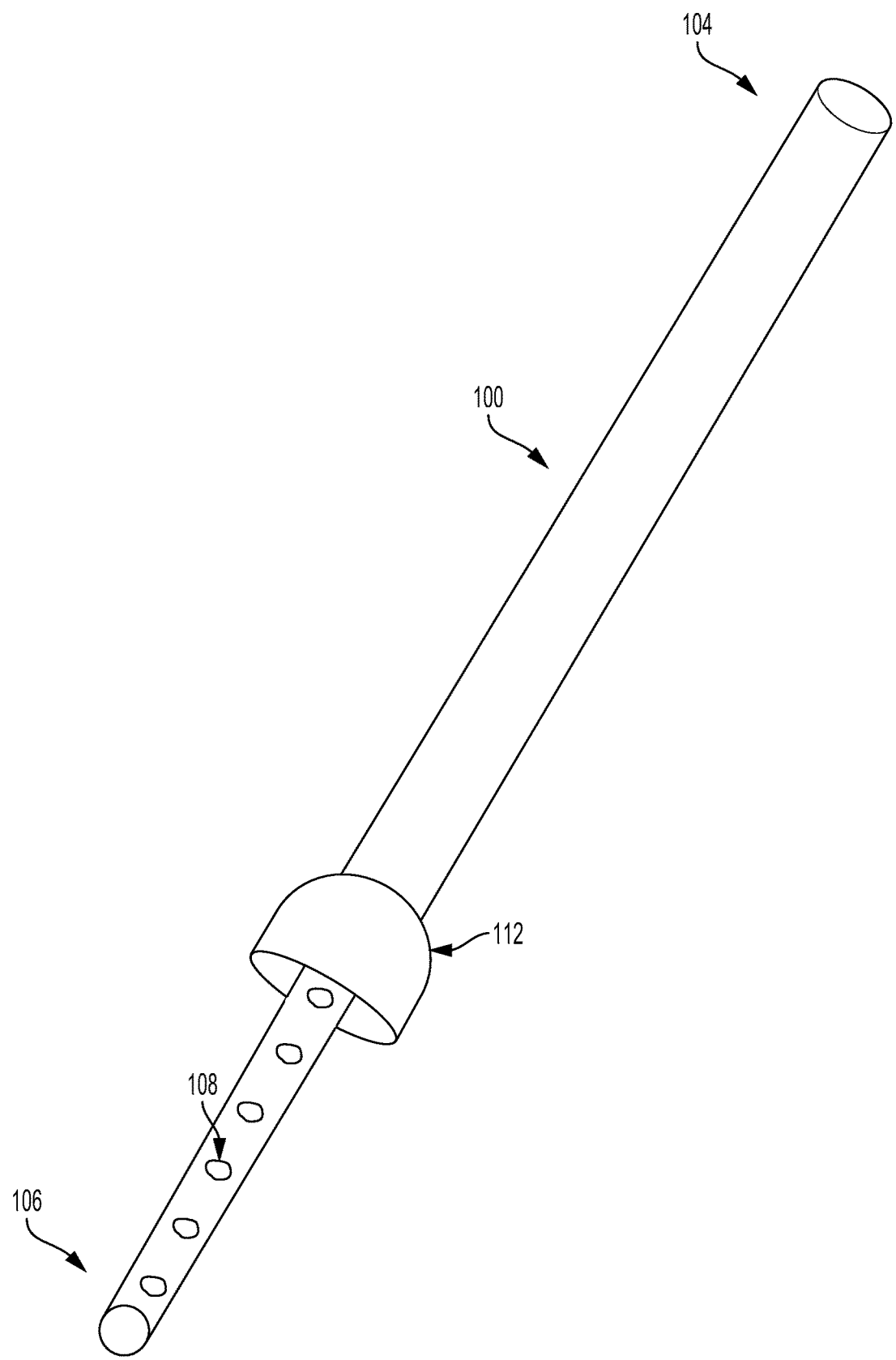
FIG. 2 is a perspective view of an alternate embodiment of the catheter of the present disclosure.

In another embodiment, shown in FIG. 2, the 3D shape 110 of the distal end 106 of the catheter 100 includes a flap 112. Similar to the embodiment shown in FIG. 1, the flap 112 is also configured to protect the proximal holes or entrance ports 108 of the catheter 100 from blockage/occlusion. In this embodiment, the catheter 100 may have at least two apertures 103 (shown in FIGS. 5A-5C) arranged in the tube body 102 between the proximal end 104 and the distal end 106. In some examples, the tube body may include additional apertures 103. In one embodiment, the flap 112 is attached to the catheter 100 through an intradiameter or intraluminal catheter 101 (shown in FIGS. 5A-5D) that allows the introduction of the protective flap 112 through the apertures 103. The catheter 100 is slid over the intradiameter catheter 101. Once the correct orientation is reached, the flap 112 can erupt from the apertures 103 located in the tube body 102 of the catheter 100 and extend outwardly around the tube body 102 so as to cover at least one of the plurality of ports 108 located near the proximal end 104 of the tube body. In addition to the flap 112, the catheter 100 may also include the 3D shape 110 at the distal end that shapes back to protect the entrance ports 108 from external obstruction, such as shown in FIG. 1.

In another embodiment, the flap 112 can be attached to a string or wire (not shown) that allows for the flap to deploy upon insertion. In this embodiment, a pre-built strap is fixed under a string or wire tension or shape memory tension, is released once the catheter is in the correct position. The flap 112 protects one or more entrance ports 108 located closest to the proximal end 104 of the catheter from outside obstruction.

In one embodiment, the flap 112 may be constructed of shape memory material. It should be understood that the flap 112 could be constructed of any biocompatible material suitable for medical use. In some embodiments, the flap 112 is constructed of the same material as the tube body 102 of the catheter 100. In alternate embodiments, the flap 112 is constructed of a different material than the tube body 102.

The drainage and/or infusion catheter and associated components of the present disclosure may be made of any biocompatible material suitable for medical use. In certain embodiments, the material, or combination of materials, meet the requirements as outlined above. Examples include, but are not limited to, (a) polyurethanes, including but not limited to, polycarbonate-based polyurethanes, polyether-based polyurethanes (e.g., aliphatic, aromatic, etc.), and thermoplastic polyurethanes (e.g., polyvinyl chloride (PVC), etc.); (b) polyamides; (c) fluoropolymers, including but not limited to, polytetrafluoroethylene (PTFE), FEP, ETFE, PFA and MFA; (d) polyolefins (e.g., high density polyethylene, etc.); (e) polyimides; (f) thermoplastic polymers, such as polyaryletherketone (PAEK) and polyether ether ketone (PEEK); (g) polycarbonate; (h) polycarbonate urethane; (i) silicone; (j) acrylic compounds; (k) thermoplastic polyesters; (l) polypropylene; (m) low-density polyethylenes; (n) nylon; (o) sulfone resins; (p) high density polyethylenes; (q) silicone, and silicone-based materials and (r) other synthetic biocompatible polymers; and combinations thereof.

In certain embodiments the drainage and/or infusion catheter comprises a shape memory material. In some embodiments, the shape memory material comprises a shape memory alloy(s). In certain embodiments, the shape memory alloy is selected from the group consisting of NiTi, CuZn, AuCd, CuSn, TiPd, NiAl, InTi, NiTiCu and CuZnAl. In other embodiments, the shape memory material comprises a shape memory polymer. In certain embodiments, the shape memory polymer is selected from the group consisting of poly(c-caprolactone) dimethacrylate, n-butyl acrylate, star-shaped oligoesters of rac-dilactide and diglyceride, multiblock copolyesters from poly(ε-caprolactone) and PEG, oligo (ε-caprolactone) diols, oligo (p-dioxanone) diols, diisocyanate, multiblock copolymers containing poly(L-lactide), poly [glycolide-co-(ε-caprolactone)]-segments, and combinations thereof.

The drainage and/or infusion catheters of the present disclosure may further comprise an additive. The additive can be in the form of a coating or embedded within the catheter material itself. For example, in some embodiments, the inflow catheter may be capable of being made radiopaque. A typical way of accomplishing this is by compounding in radiopaque filler. The filler and the amount of it used should not negatively affect the physical and mechanical characteristics of the polymer. Further, the percentage of radiopaque filler should be sufficient to show up on x-ray and on fluoroscope. For example, thermoplastic polyurethanes can be loaded with up to 40% by weight of radiopaque filler.

The amount and type of radiopaque filler influence both the effect on physical properties and x-ray response and thus is dependent on the specific use of the catheter, however, once known can be readily determined by one skilled in the art. For example, barium sulfate has a lower x-ray response than bismuth subcarbonate. It takes more barium sulfate to get the same x-ray response as bismuth subcarbonate. Because the density of barium sulfate is about half that of bismuth subcarbonate, it takes up more volume in the polymer mix. The greater the volume that the radiopaque filler takes up in the polymer mix, the greater the reduction in physical properties. In some embodiments, the occlusion-resistant catheter of the present disclosure further comprises a radiopaque filler selected from the group consisting of bismuth subcarbonate, barium sulfate, tantalum, and combinations thereof.

In other embodiments, the material selected for the drainage and/or infusion catheter of the present disclosure is able to accept coatings. In some embodiments, the coatings consist of a moisture-sensitive polymer that becomes lubricious when wetted by blood. Such coatings may include, but are not limited to, bactericides, antibodies, lubricants, and combinations thereof.

In some cases, the surface of the drainage and/or infusion catheter will need to be treated so that the coatings will adhere. In such cases, to achieve good adhesion, the surface of the catheter may have to be treated. Examples of treatments are chemical etchants, plasma treatments, and corona surface treatments.

The drainage and/or infusion catheters of the present disclosure may be manufactured by any number of methods, including, but not limited to, injection molding, 3D-printing, and the like.

The drainage and/or infusion catheters of the present disclosure may comprise various other alterations/embodiments that are intended to fall within the scope of the present disclosure. Such embodiments include, but are not limited to, the following: (a) having the drainage and/or infusion catheter comprise various durometers; (b) having the drainage and/or infusion catheter and various components comprise of bioabsorbable materials; and (c) having the drainage and/or infusion catheter and components comprise different materials (e.g., the primary length of the catheter comprises silicone and the distal end comprising a secondary material, such as a shape memory polymer).

Figure 3:
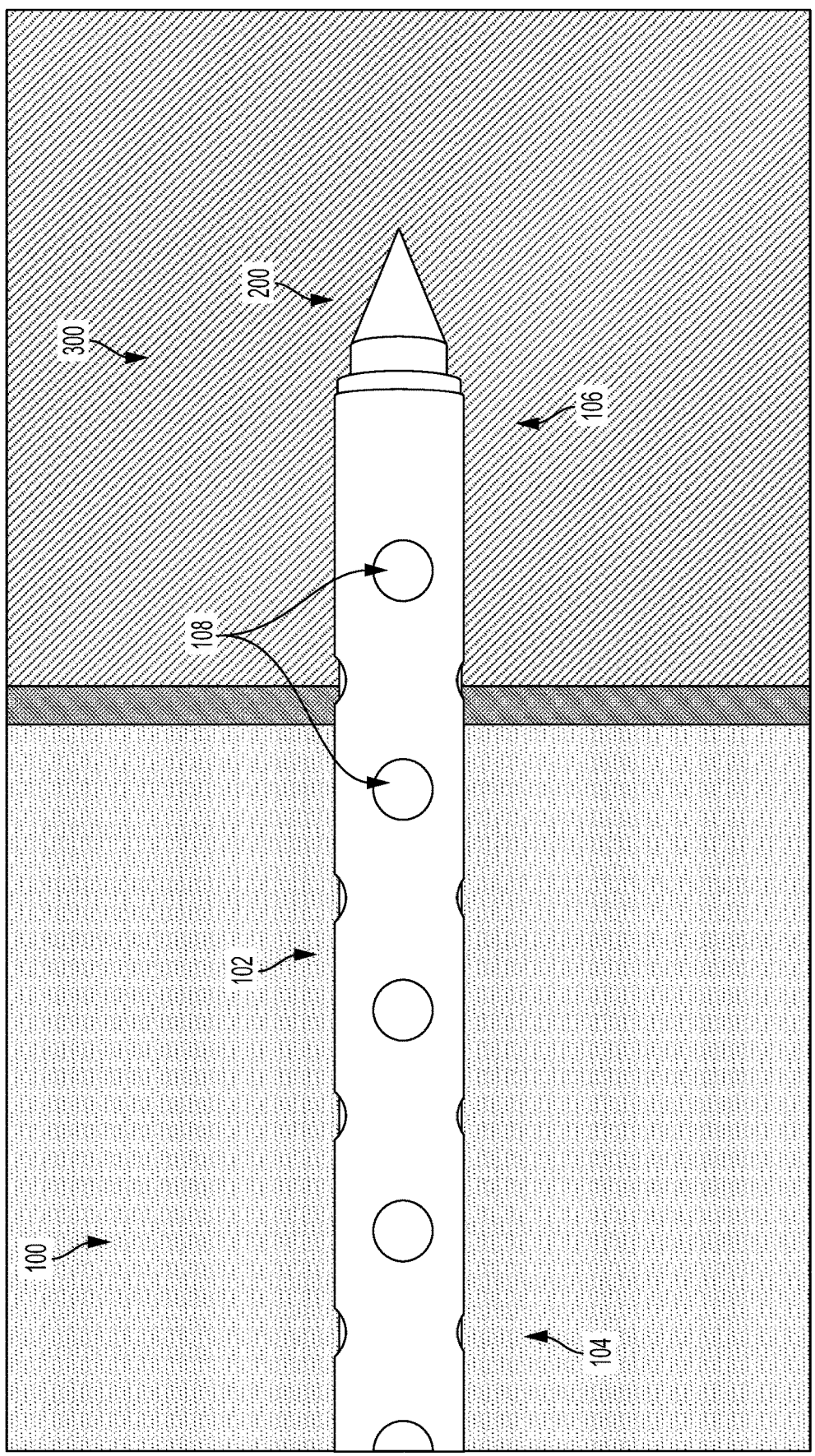
FIG. 3 is a perspective view of the catheter shown in FIG. 1 with an introducer being inserted therethrough.

In another embodiment, referring to FIG. 3, the drainage and/or infusion catheter may be inserted into a cavity 300 of a patient or subject using an introducer 200. This can be done with or without the use of a wire and dilators (Seldinger technique) or by direct placement. When the introducer 200 is placed inside the tube body 102 from the proximal end 104 and thread through the tube body, the 3D shape or configuration 110 deforms at the distal end to provide easier insertion of the catheter 100 into the ventricle. For example, as shown in FIG. 3, when the introducer 200 is placed inside the tube body 102 from the proximal end 104, the distal end 106 straightens (i.e., the 3D configuration is deformed) to provide easier insertion of the catheter into the cavity 300. As shown in FIGS. 4A-4F, when the introducer 200 is removed, the distal end 106 returns to its original 3D shape 110.

The introducer 200 may comprise any length sufficient to extend through the tube body 102 and deform the 3D shape 110 at the distal end 106. In some embodiments, the overall length of the introducer 200 ranges from about 5 cm to about 60 cm. In other embodiments, the overall length of the introducer 200 ranges from about 8 cm to about 50 cm. In yet other embodiments, the overall length of the introducer 200 ranges from about 10 cm to about 46 cm. In some embodiments, the introducer 200 is cylindrical in shape. However, it should be understood that the introducer 200 can be of any general shape, such as rectangular, cylindrical, triangular, square and the like, so as to fit within the tube body 102 of the catheter 100.

In some embodiments, the diameter/width of the introducer ranges from about 0.1 mm to about 2 mm across. In other embodiments, the diameter/width of the introducer ranges from about 0.3 to about 1.5 mm across. In yet other embodiments, the diameter/width of the introducer ranges from about 0.5 mm to about 1.0 mm across.

The introducer 200 may comprise varying material properties, including but not limited to, metal, polymer of various durometers, polymer or metal coatings, and the like.

For removal of the catheter 100, the introducer 200 is threaded through the catheter to the first turn of the coil. The catheter 100 is then retracted and unwinds over the rigid introducer 200. Once fully straightened, the catheter and introducer are withdrawn from the cavity together.

Another aspect of the present disclosure provides a method for inserting the drainage and/or infusion catheter 100 as described herein into a cavity 300 a subject. The catheter 100 can be used in any cavity of a subject to drain fluid or infuse agents to a subject in need thereof. Suitable agents for infusion include, but are not limited to, drugs, chemotherapeutic agents, biological fluids, blood, saline, and the like. In some embodiments, the cavity comprises a ventricle and the drainage and/or infusion catheter drains CSF. In another embodiment, the cavity comprises an abdominal cavity, the gallbladder, pleural space, and others.

In yet another embodiment, the cavity comprises a vessel in which the catheter is used for infusion of an agent.

Figure 4A:
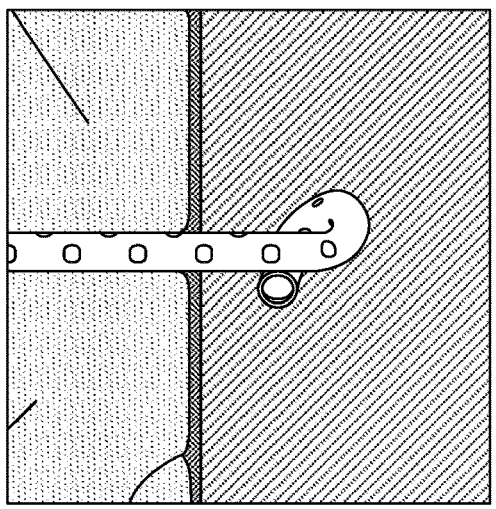
FIGS. 4A-4F show the catheter of FIG. 1 being inserted into a subject.
Figure 4B:
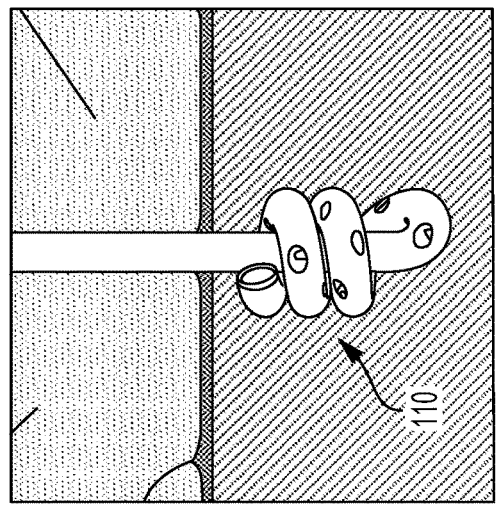
Figure 4C:
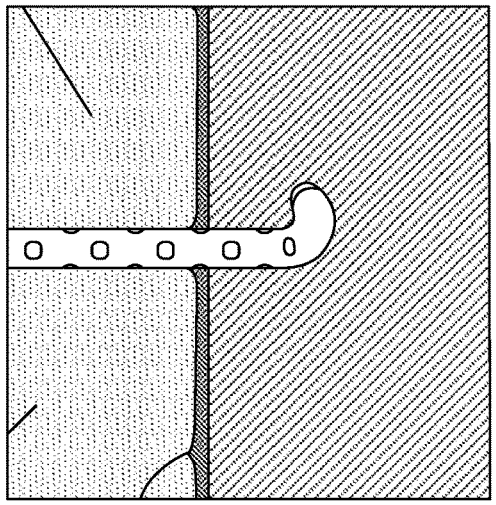
Figure 4D:
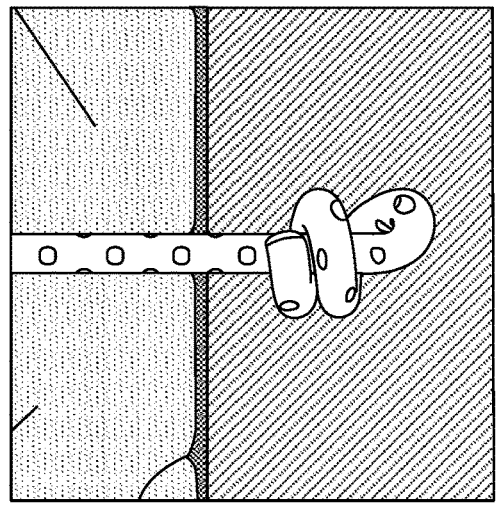
Figure 4E:
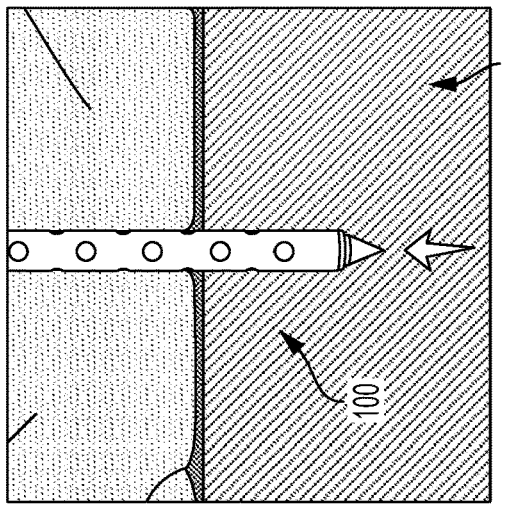

FIGS. 3 and 4A-4F show the steps involved in such a method. The method includes inserting the introducer 200 inside the tube body 102 of the drainage and/or infusion catheter 100 such that the 3D shape 110 at the distal end 106 is deformed (e.g., straightened), and then inserting the drainage and/or infusion catheter 100 into a cavity 300, as shown in FIG. 3. Next, as shown in FIG. 4A, the inserter 200 is removed from the drainage and/or infusion catheter 100 back through the proximal end 104, as indicated by the arrow. As the introducer 200 is withdrawn from the catheter 100, the distal end 106 of the catheter begins to deform/re-form back into its 3D shape 110, as shown in FIGS. 4B-4E. In some embodiments, a user can draw the introducer 200 partially out of the tube body 102, which allows only a portion of the distal end 106 to reconfigure into the 3D shape 110. Doing so allows for more space for more insertion of the catheter within the cavity 300 of the subject.

Figure 4F:
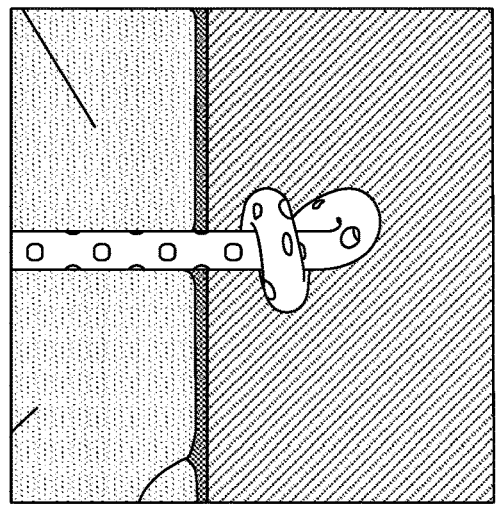

When the introducer 200 is fully removed, the 3D shape 110 is re-formed at the distal end 106 of the tube body 102, as shown in FIG. 4F. Additionally, one or more entrance ports 108 located closest to the proximal end 104 of the catheter 100 are covered/protected by the 3D shape 110.

The method further provides the optional step of attaching the drainage and/or infusion catheter available at different lengths to suction or infusion ports or part of a shunt system with or without a valve.

Referring now to FIGS. 5A-5D, the steps of inserting a catheter with a flap 112 are shown. The catheter 100 can be directly placed in open procedures, or inserted over a wire and/or introducer as discussed above. FIG. 5A shows the catheter 100 with apertures 103 and entrance ports 108. In FIG. 5B, the catheter 100 is slid over the intradiameter catheter 101 having a flap 112. Once the correct orientation is reached, the flap 112 can erupt through the apertures 103, as shown in FIG. 5C. The flap 112 then may spread around the catheter 100, creating a protective shield around one or more entrance ports 108 located closest to the proximal end 104, as shown in FIG. 5D and FIG. 2.

Figure 6:
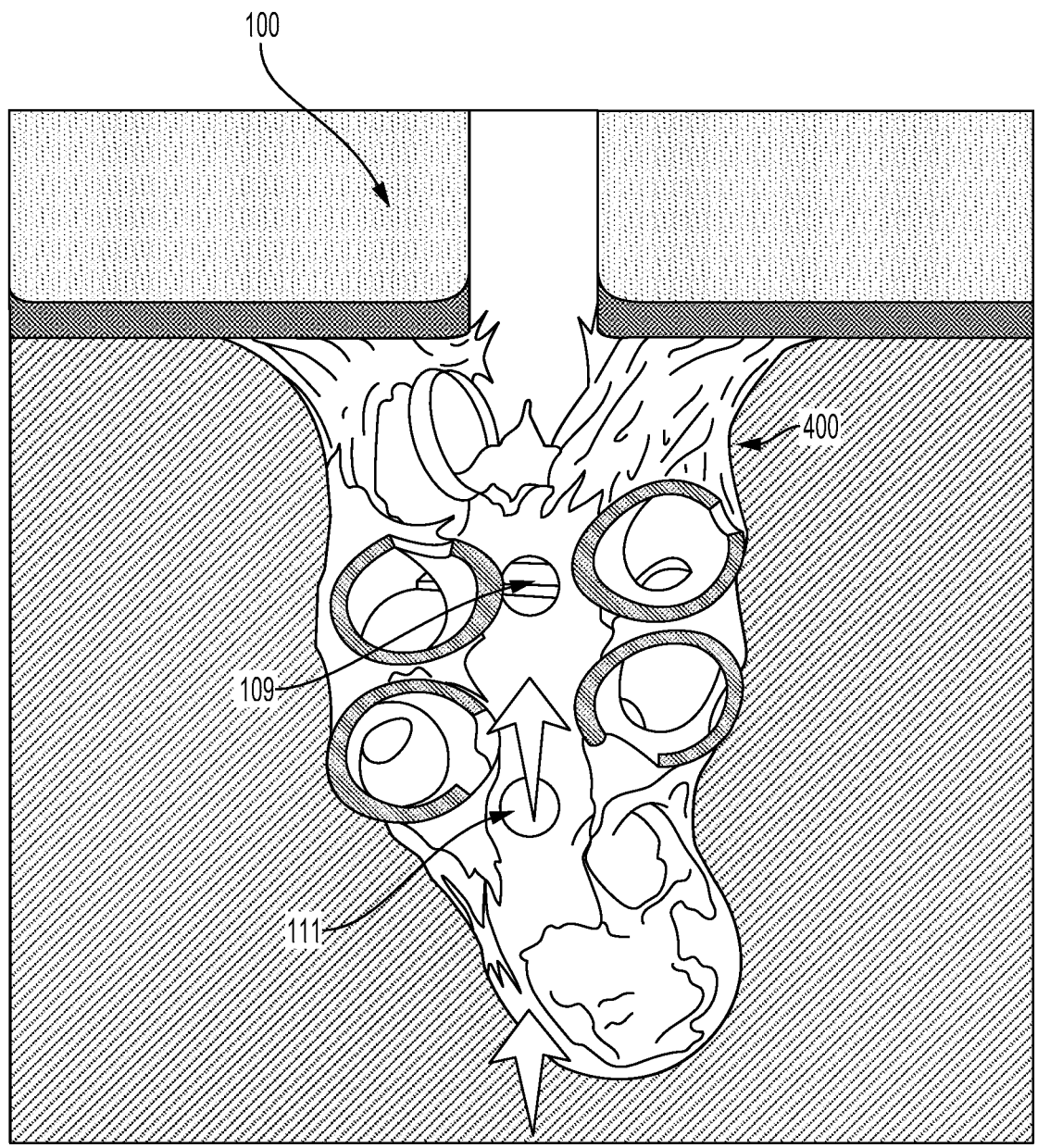
FIG. 6 is a perspective view of the catheter of FIG. 1 inserted in a subject over time.

FIG. 6 shows the catheter 100 of the present application in use after insertion. Although many of the plurality of entrance ports 108 are blocked, such as by choroid plexus, surrounding organs, clots or other, 400, two entrance ports 109, 111 which are located closest to the proximal end 104 of the catheter 100 are still open since they are covered/protected by the 3D shape 110. Thus, the original catheter 100 maintains its proper function and does not require reparation or replacement.

Another aspect of the present disclosure provides a kit comprising a drainage catheter as provided herein, an introducer and instructions for use. In some embodiments, the kit may further comprise items selected from the group consisting of additional tubing, sterile gloves, sterilization pads, additional members configured to be inserted into the drainage catheter such as diagnostic testing implements or devices, structural support elements, or other devices and implements used in conjunction with drainage catheters and combinations thereof.

Any patents or publications mentioned in this specification are indicative of the levels of those skilled in the art to which the invention pertains. These patents and publications are herein incorporated by reference to the same extent as if each individual publication was specifically and individually indicated to be incorporated by reference. In case of conflict, the present specification, including definitions, will control.

One skilled in the art will readily appreciate that the present disclosure is well adapted to carry out the objects and obtain the ends and advantages mentioned, as well as those inherent therein. The present disclosure described herein is presently representative of preferred embodiments, are exemplary, and are not intended as limitations on the scope of the invention. Changes therein and other uses will occur to those skilled in the art which are encompassed within the spirit of the disclosure as defined by the scope of the claims.

The invention claimed is:

1. A method for inserting a drainage or infusion catheter into a cavity of a subject comprising:
   providing a catheter comprising:
   a tube body defining a passageway therethrough, the tube body having a proximal end and a distal end, and a non-deformed central region extending between the proximal end and the distal end; and
   a plurality of ports arranged along the tube body from the distal end to the non-deformed central region, the plurality of ports extending into the non-deformed central region;
   wherein the distal end of the tube body is configured to be deformed around the non-deformed central region in a 3D shape so as to surround at least one of the plurality of ports located in the non-deformed central region of the tube body;
   inserting an introducer within the tube body of the catheter such that the 3D shape at the distal end is straightened by the introducer;
   inserting the catheter into the cavity; and
   removing the introducer from the catheter in a removal direction such that when the introducer is removed, the distal end of the tube body deforms backward at least in the removal direction with respect to the non-deformed central region and re-forms into the 3D shape and surrounds at least one of the plurality of ports located in the non-deformed central region of the tube body.

2. The method of claim 1, further comprising attaching the catheter to an external drainage or infusion apparatus, or to a shunt-valve system.

3. The method of claim 1, in which the cavity comprises a ventricle and the drainage catheter drains cerebral spinal fluid.

4. The method of claim 1, in which the cavity comprises an abdominal cavity, a gallbladder, or a pleural space.

5. The method of claim 1, in which the cavity comprises a heart chamber or a pericardial space.

6. The method of claim 1, in which the cavity comprises a blood vessel for the drainage or circulation of blood or infusion of blood or an agent.

7. The method of claim 6, in which the agent is selected from the group consisting of drugs, chemotherapeutic agents, biological agents, blood, saline, and dialysis fluid.

8. The method of claim 1, wherein the 3D shape comprises one of a loop, a "j", a knot, a spiral, a flap, or a coil, or combinations thereof.

9. The method of claim 1, wherein the catheter comprises a shape memory material.

10. A drainage or infusion catheter comprising:
    a tube body defining a passageway therethrough, the tube body having a proximal end and a distal end, and a non-deformed central region extending between the proximal end and the distal end; and a plurality of ports arranged along the tube body from the distal end to the non-deformed central region, the plurality of ports extending into the non-deformed central region;

wherein the distal end of the tube body is configured to deform backward at least in a direction toward and around the non-deformed central region into a substantially spiral shape so as to surround at least one of the plurality of ports located in the non-deformed central region of the tube body; and wherein during insertion of the drainage or infusion catheter, the substantially spiral shape of the distal end of the tube body is configured to straighten into a substantially linear shape.

11. The drainage or infusion catheter according to claim 10, further comprising a flap being configured to extend outwardly around the tube body.

12. The drainage or infusion catheter according to claim 10, wherein the tube body has a length of about 5 cm to about 100 cm.

13. The drainage or infusion catheter according to claim 10, wherein the tube body has an outer diameter of about 1 mm to about 80 mm.

14. The drainage or infusion catheter according to claim 10, wherein the plurality of ports has a width of about 0.1 mm to about 2 mm and a length of about 1.5 mm to about 12 mm.

15. The drainage or infusion catheter according to claim 10, wherein the plurality of ports comprises at least forty ports.

16. The drainage or infusion catheter according to claim 10, wherein the catheter comprises a shape memory material.

17. The drainage or infusion catheter according to claim 16, wherein the shape memory material comprises one of a shape memory alloy and a shape memory polymer.

18. The drainage or infusion catheter of claim 17, in which the shape memory polymer is selected from the group consisting of poly(c-caprolactone) dimethacrylate, n-butyl acrylate, star-shaped oligoesters of rac-dilactide and diglyceride, multiblock copolyesters from poly(c-caprolactone) and PEG, oligo (c-caprolactone) diols, oligo (p-dioxanone) diols, diisocyanate, multiblock copolymers containing poly (L-lactide), poly [glycolide-co-(c-caprolactone)]-segments, and combinations thereof.

19. The drainage or infusion catheter of claim 17, in which the shape memory alloy is selected from the group consisting of NiTi, CuZn, AuCd, CuSn, TiPd, NiAl, InTi, NiTiCu and CuZnAl.

20. A kit for treating a subject comprising a drainage or infusion catheter according to claim 10, an introducer, and instructions for use.

* * * * *